United States Patent [19]

Lash et al.

[11] Patent Number: 4,558,693
[45] Date of Patent: Dec. 17, 1985

[54] PENILE IMPLANT

[76] Inventors: Harvey Lash, 2309 Byron; Morris Kibrick, 3921 Nelson Dr., both of Palo Alto, Calif. 94306

[21] Appl. No.: 527,703

[22] Filed: Aug. 29, 1983

[51] Int. Cl.⁴ .............................................. A61F 5/00
[52] U.S. Cl. .......................................... 128/79; 623/11
[58] Field of Search .................................. 128/79; 3/1

[56] References Cited

U.S. PATENT DOCUMENTS

| | | | |
|---|---|---|---|
| 4,201,202 | 5/1980 | Finney et al. | 128/79 |
| 4,224,934 | 9/1980 | Scott et al. | 128/79 |
| 4,353,360 | 10/1982 | Finney et al. | 128/79 |
| 4,399,812 | 8/1983 | Whitehead | 128/79 |
| 4,411,261 | 10/1983 | Finney | 128/79 |

*Primary Examiner*—Dalton L. Truluck
*Attorney, Agent, or Firm*—Stephen P. Fox; Allston L. Jones

[57] ABSTRACT

The prosthesis comprises a flexible rod, surrounded along approximately two-thirds of its length by an inflatable balloon, which is implanted centrally within the two corpora cavernosa of the penis and replacing the function of same. To supply fluid to the inflatable balloon there is a reservoir that is implanted within the scrotal sac of the patient. Located in a tube between the reservoir and the balloon portion of the implant is a pinch valve for maintaining the fluid within either the balloon portion or the reservoir under the control of the patient. To effect erection of the penis, the pinch valve is pinched while the reservoir is squeezed, forcing the hydraulic fluid into the balloon portion of the implant. When it is desired to depressurize the implant, the pinch valve is again pinched and the fluid under pressure will then return to the unpressurized reservoir.

11 Claims, 5 Drawing Figures

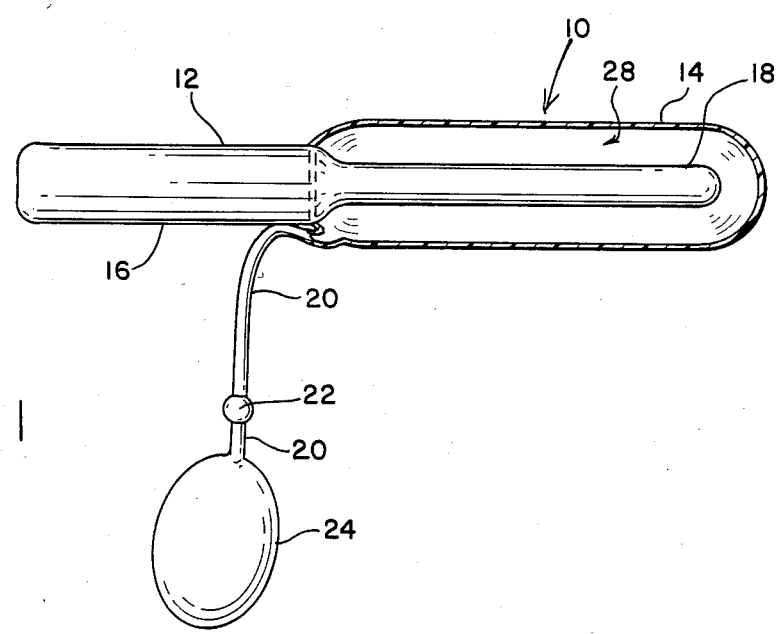
FIG. 1
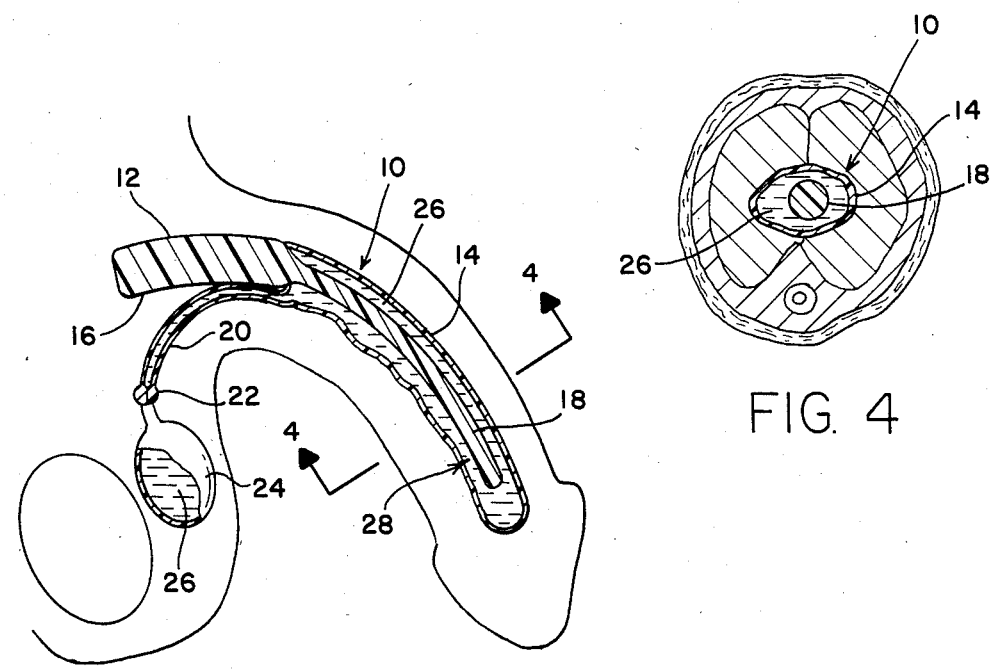
FIG. 2
FIG. 4

PENILE IMPLANT

BACKGROUND OF THE INVENTION

This invention relates to an implantable prosthesis, namely a penile prosthesis designed to overcome erectile impotence.

The prior art includes several different penile prosthesis design approaches. The first type is a pair of rods, each of a suitable stiffness, which are implanted into the corpora cavernosum of the penis. U.S. Pat. No. 3,893,456 is representative of these devices. This approach is disadvantageous for several reasons. The rod has permanent stiffness which could be a source of embarrassment, or pain if the patient attempted to depress the penis in order to conceal it. Additionally, the rod type prosthesis is incapable of appreciably increasing the length or girth of the penis.

The second type of penile prosthesis is of the inflatable variety. The most common of this design includes two long inflatable tubes, or balloons, which are implanted in the corpora cavernosum of the penis. The various two balloon designs include either one or two fluid reservoirs, tubing, valves, and pump to complete the system. The reservoirs and valves are generally implanted in the retropubic space, and the pump in the scrotal sac (U.S. Pat. Nos. 3,853,122; 4,009,711; 4,224,934 and 4,235,227), other designs show them implanted in the abdominal cavity (U.S. Pat. Nos. 3,853,122 and 3,954,102). As a result of the lack of rigidity of the balloons, a large amount of fluid is necessary to pressurize the balloons to obtain the needed degree of penile rigidity, which in turn requires a large reservoir system.

U.S. Pat. Nos. 4,318,396 and 4,353,360 also incorporate the balloon design in a double or single implant configuration, with the fluid reservoir located in the penis as well. In the prosthesis of U.S. Pat. No. 4,318,396, the balloon is made from a rubberized fabric sealed to stiff stem and tip portions at both the proximal and distal ends, respectively. Since the balloon is made of a rubberized fabric there is no appreciable stretching of same when it is pressurized. Further, a magnetic latching clamp is shown which squeezes the prosthesis and the penis over a portion of its length to achieve pressurization of the fluid within to provide the desired erection. This clamp adds unnecessary weight and discomfort to the patient. The prosthesis of U.S. Pat. No. 4,353,360 is a design wherein a first balloon is enclosed within a second balloon with both in communication with an in-line, in-penis valve. These also have the same problems mentioned above for the other balloon type penile prosthesis.

The third type of penile prosthesis is one wherein a rod and a balloon are combined. U.S. Pat. No. 4,201,202 to Finney, et al. shows such a device. However, this design requires the implantation of two separate units each with its own reservoir and valve. The balloon consists of a silicone coated woven fabric around a rod which extends beyond the balloon at both the distal and proximal ends, thereof. This design therefore can only provide expansion axially, not longitudinally, and, the sealing of the balloon with the rod at two locations greatly increases the likelihood of leaks.

In each of the double implant balloon designs a leak in one side will result in erectile pressurization in only one side of the penis. This will yield unsatisfactory performance and a distorted appearance which can only be corrected by another surgery.

It is desirable to have a single implantation design that minimizes the surgery, is inflatable with a small volume of fluid from a single reservoir to minimize the reservoir size, and includes a rod which would provide acceptable performance should the hydraulic portion of the prothesis fail. It is believed that the present invention provides such a device.

SUMMARY OF THE INVENTION

As illustrated by the preferred embodiment, the present invention provides a penile prosthesis to correct erectile impotence. The prosthesis of the present invention includes a single flexible rod, surrounded along approximately two-thirds of its length by an inflatable balloon. The rod and balloon combination is implanted in the penis. The balloon is connected to a reservoir implanted in the scrotal sac by means of a tube containing a control valve. The material for such a prosthesis is silicone rubber or another material with similar properties. The shorter proximal portion of the flexible silicone rod can be cut to adjust the length of the prosthesis to the length of the penis of the patient when it is implanted into the proximal end of the corpora cavernosum with the balloon end of the device situated distally. The silicone balloon is bonded in a fluid tight manner to prevent fluid leakage when pressurized with the fluid, resulting in increased length, girth and rigidity of the penis when erect. The silicone tube is cemented to the rod as shown to prevent tearing during insertion of the prosthesis and to minimize weakening of the tunica albugina. The device is designed to operate in the following manner: When erection is desired, the valve is squeezed open by one hand, thus permitting fluid to be forced into the penile balloon by squeezing the reservoir within the scrotal sac, and then releasing the valve for the purpose of closure. When erection is no longer desired, the valve is once again squeezed open, permitting the solution to return to the reservoir from the balloon. Additionally, the flexible rod in the distal portion (the one purpose of which is to minimize the amount of fluid required for the balloon and thus for the reservoir) would permit vaginal penetration in the unlikely event of leakage occuring in the system.

DESCRIPTION OF THE FIGURES

Specific details relative to the subject invention will be fully described below with reference to the accompanying drawings in which:

FIG. 1 shows a plan view of the penile prosthesis of the present invention.

FIG. 2 is a partial sectional view of the penile prosthesis of FIG. 1 in a deflated condition as surgically implanted in a male wherein the penis is in a semi-flaccid state.

FIG. 4 is a cross-section along line 4—4 in FIG. 2.

DESCRIPTION OF THE PREFERRED EMBODIMENT

Figure 3:
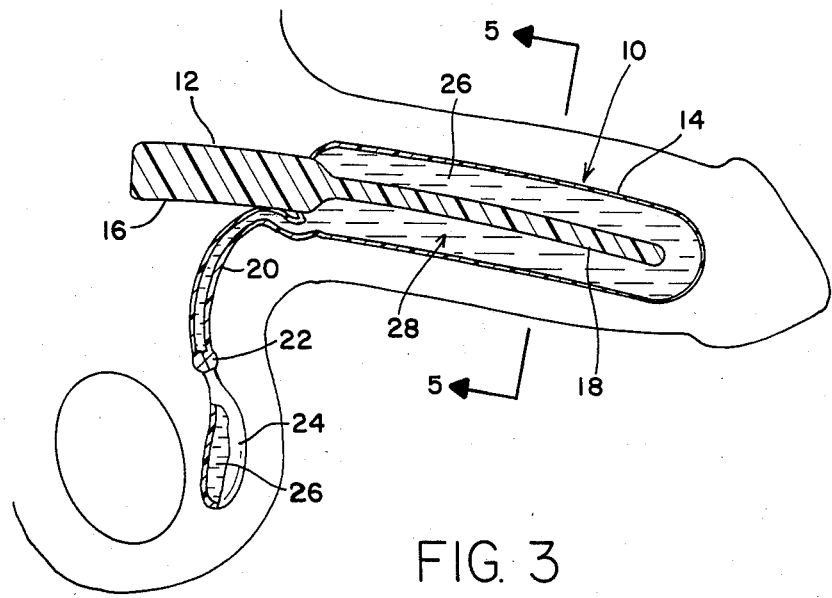
FIG. 3 is a view similar to FIG. 2 with the prosthesis fully pressurized.

FIG. 1 shows a plan side view of a penile prosthesis 10 of the present invention fully inflated. Penile prosthesis 10 includes a single flexible rod 12, a balloon 14 surrounding a portion of rod 12 and a reservoir 24 connected to balloon 14 via flexible tube 20. Flexible rod 12 includes a proximal portion 16 making up approximately one-third of its length and a distal portion 18 making up the balance of its length. Proximal portion 16 has a diameter which is approximately 1½ times the diameter of distal portion 18. In the transition region between the two portions of flexible rod 12, balloon 14 is sealed to rod 12 to form cavity 28. Cavity 28 and reservoir 24 are designed to contain hydraulic fluid for transfer as desired between these two areas by means of a squeeze type valve 22, and a portion of tube 20 is cemented to the proximal portion 16 of rod 12 to prevent it from being torn from balloon 14 during the implantation of the prosthesis and to minimize injury to delicate penile tissues.

As shown in FIGS. 2-5 the distal portion 18 of rod 12 surrounded by balloon 14 is inserted centrally within the two halves of the corpora cavernosum of the penis. The proximal portion 16 of rod 12 is implanted in the root end of the corpora cavernosum to support the implant. The reservoir 24 and valve 22 are implanted in the scrotal sac. The reservoir 24 contains a suitable fluid 26, typically a 0.9% salt in pure water (saline solution) and is connected via tube 20 to balloon 14 implanted within the penis. For controlling the flow of fluid between reservoir 24 and balloon 14, suitable valve means 22 (such as Hyer Schulte Rosen type or Jenny type) which allows fluid 26 to flow in one direction or the other as the patient may desire, only when valve 22 is pinched through the scrotal sac.

Figure 5:
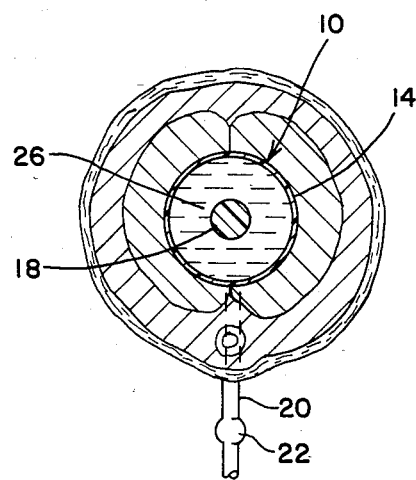
FIG. 5 is a view taken along line 5—5 in FIG. 3.

FIGS. 2 and 4 show the prosthesis 10 in the nonpressurized condition. In this mode the pressurizing fluid 26 is substantially all in reservoir 24 with valve 22 closed. FIGS. 3 and 5 show the condition where the patient has caused the prosthesis 10 to be pressurized by forcing fluid 26 from reservoir 24 into cavity 28 within balloon 14. The pressurization of the prosthesis 10 is done by the patient pinching valve 22 while squeezing reservoir 24 and then releasing valve 22 before reservoir 24 is released. When valve 22 is no longer being pinched the fluid is blocked from returning to reservoir 24. When pressurization is no longer desired, the patient merely reverses this process by again pinching valve 22, and squeezing the penis to allow fluid 26 to return to reservoir 24, thus depressurizing the cavity 28 within the prosthesis 10 and allowing the penis to return to the flaccid state.

With the possible exception of valve 22, penile prosthesis 10 is made of a plastic material such as silicone. The rod 12 of the present invention has a Shore A hardness of 75-85 in its entirety, and the balloon 14 has a Shore A hardness of 25-35. The rod 12 therefore can be seen to be a fairly flexible and soft, thus avoiding any problems which exist with the stiff rods used in some of the prior art prostheses, and the balloon is seen as being somewhat stronger than a typical novelty balloon. With this design it is also anticipated that hydraulic fluid 26 will be sealed within the unit at the time of manufacture, unlike some of the prior art balloon type protheses. As a result of the combination rod/balloon design of the present invention the volume of fluid necessary to pressurize the prothesis to provide sufficient stiffness to the penis is greatly reduced. Thus, it is possible to make the size of reservoir 24 much smaller than those of the prior art. Also, this design, unlike the prior art, provides a means for enlarging the penis both longitudinally and axially during pressurization of the prosthesis to effect the desired erection. In the unlikely event that the balloon 14 or the hydraulic portions of the prothesis were to rupture and the hydraulic fluid 26 to leak, the rod 12 would still provide enough penile stiffness to effect vaginal penetration, therefore avoiding additional surgeries to restore desired penile function.

IMPLANTING PROCEDURE

The patient is prepared and draped in the usual fashion and either local or general anasthesia may be used. A 3 cm. longitudinal incision is then made on the middle third of the dorsum of the penile shaft in the midline. Buck's fascia is traversed, the tunica albuginea is opened (attempting to maintain a midline position) and the corpora cavernosum is split. A tunnel is developed distally, as well as proximally, care being exercised to dissect dorsally, just below the tunica albuginea to protect the underlying urethra. Blunt finger dissection in the intertesticular scrotal tissues prepares space for the reservoir of the prosthesis. The prosthesis is then adjusted to the proper length by measuring the distance from the pubis to the proximal glans with the penile shaft under slight tension, and then cutting the proximal portion of the rod 12 to length. The cut end is then sanded to remove any sharp edges, and the distal portion is then placed between the corpora, after which the reservoir is inserted into the scrotal pocket. Closure of the tunica albuginea and then Buck's fascia is accomplished.

While there has been shown and described the preferred embodiment of the present invention, it will be apparent to those skilled in the art that many changes and modifications may be made without departing from the invention in its broader aspects. Therefore, the appended claims are intended to cover all such modifications and changes that fall within the true spirit and scope of the invention.

We claim:
1. A penile prosthesis comprising:
an elongated flexible rod, having a proximal portion and a distal portion, the distal portion having a greater length and a smaller diameter than the proximal portion said distal and proximal portions meeting in a sloping shoulder;
an elongated, omni-directionally elastic balloon when in the quiescent state having an inner diameter that is at least as large as the diameter of distal portion of the rod, said balloon extending beyond the end of and surrounding the distal portion of the rod to form a cavity therebetween and having its open end sealed to said proximal portion at the shoulder;
a reservoir means for containing a fluid and for pressurizing a fluid within the cavity within the balloon;
fluid transfer means for transporting a fluid between the balloon and the reservoir means; and
valve means for controlling the flow of fluid between the balloon and the reservoir;
said rod and balloon combination disposed to be installed between the two corpora cavernosum extending from the pubis to the proximal glans with the distal portion oriented toward the glans.
2. A penile prosthesis as in claim 1 wherein said valve means includes a pinch valve which permits the flow of fluid therethrough only while being pinched.
3. A penile prosthesis as in claim 1 wherein the rod, the balloon, the reservoir means and the transfer means are each made of silicone rubber.
4. A penile prosthesis as in claim 3 wherein the rod has a Shore A hardness of about 75 throughout both its proximal and distal portions.

5. A penile prosthesis as in claim 3 wherein the balloon has a Shore A hardness of about 30.

6. A penile prosthesis as in claim 1 wherein the portion of the fluid transfer means adjacent to its interconnection with the balloon is connected to the proximal portion of the rod to prevent tearing during implantation of the prosthesis and to minimize injury to delicate penile tissues.

7. A penile prosthesis as in claim 1 wherein the rod has sufficient stiffness to achieve vaginal penetration without pressurization of the balloon and flexible enough to prevent embarrassment of the patient under normal circumstances.

8. A penile prosthesis as in claim 1 wherein the size of the unpressurized cavity within the balloon is minimized by maximizing the diameter of the distal end of the rod to minimize the volume of fluid necessary to pressurize the balloon and cause the desired penile erection.

9. A penile prosthesis as in claim 1 wherein the proximal portion of the rod may be cut and shaped for the actual penile length of a patient.

10. A penile prosthesis as in claim 1 wherein the length of the distal portion is at least twice the length of the proximal portion of the rod.

11. A penile prosthesis as in claim 1 wherein the diameter of the proximal portion of the rod is approximately one and a half times the diameter of its distal portion.

* * * * *